(12) United States Patent
Steinway et al.

(10) Patent No.: US 7,671,784 B2
(45) Date of Patent: Mar. 2, 2010

(54) COMPUTERIZED TOMOGRAPHY USING RADAR

(75) Inventors: William Steinway, New Smyrna Beach, FL (US); David H. Fine, Cocoa Beach, FL (US); Stephen Cole, Orlando, FL (US); Ravi K. Konduri, Heathrow, FL (US); Douglas O. Carlson, Winter Garden, FL (US); Yuriy Pylypenko, Campbell, CA (US)

(73) Assignee: L-3 Communications CyTerra Corporation, Orlando, FL (US)

( * ) Notice: Subject to any disclaimer, the term of this patent is extended or adjusted under 35 U.S.C. 154(b) by 0 days.

(21) Appl. No.: 11/852,623

(22) Filed: Sep. 10, 2007

(65) Prior Publication Data

US 2008/0169961 A1 Jul. 17, 2008

Related U.S. Application Data

(63) Continuation-in-part of application No. 11/421,013, filed on May 30, 2006, now Pat. No. 7,312,742.

(60) Provisional application No. 60/685,658, filed on May 31, 2005, provisional application No. 60/825,065, filed on Sep. 8, 2006.

(51) Int. Cl.
*G01S 13/89* (2006.01)
*G01S 13/88* (2006.01)
*G01N 22/00* (2006.01)
*G01S 13/00* (2006.01)

(52) U.S. Cl. .............................. 342/22; 342/27; 342/52; 342/59; 342/89; 342/175; 342/176; 342/179; 342/195; 600/300; 600/407; 600/430

(58) Field of Classification Search ................... 342/21, 342/22, 25 R–25 F, 59, 89, 118, 128–133, 342/175, 176, 179, 195, 27, 28, 52–55, 192–194, 342/196, 197; 600/300, 407, 424, 430, 549
See application file for complete search history.

(56) References Cited

U.S. PATENT DOCUMENTS 3,351,936 A 11/1967 Feder (Continued)

FOREIGN PATENT DOCUMENTS

WO WO 2005/119214 A1 12/2005

OTHER PUBLICATIONS

Partial International Search Report mailed Oct. 26, 2006 issued in International Application No. PCT/US2006/021345, pp. 1-2.

(Continued)

*Primary Examiner*—Bernarr E Gregory
(74) *Attorney, Agent, or Firm*—Fish & Richardson P.C.

(57) ABSTRACT

Techniques for detecting contraband are described, as are techniques for generating an image of living tissue. A location of interest relative to a target space is received, and a radar signal is transmitted in the direction of the location of interest. Portions of the radar signal are detected with multiple receiving structures. The detected portions are processed to generate information corresponding to dielectric or loss properties, the properties corresponding to particular positions within the target space. A determination is made as to whether contraband is present in the target space based on the determined properties.

25 Claims, 13 Drawing Sheets

U.S. PATENT DOCUMENTS

| | | | |
|---|---|---|---|
| 3,665,466 A | 5/1972 | Hibbard | |
| 4,774,961 A * | 10/1988 | Carr | 600/549 |
| 5,325,095 A | 6/1994 | Vadnais | |
| 5,499,029 A | 3/1996 | Bashforth | |
| 5,592,170 A | 1/1997 | Price | |
| 6,057,761 A | 5/2000 | Yuki | |
| 6,061,589 A | 5/2000 | Bridges | |
| 6,600,441 B2 | 7/2003 | Liedtke | |
| 6,664,914 B2 | 12/2003 | Longstaff | |
| 6,700,526 B2 | 3/2004 | Witten | |
| 6,831,590 B1 | 12/2004 | Steinway | |
| 6,965,340 B1 | 11/2005 | Baharav | |
| 6,967,612 B1 | 11/2005 | Gorman | |
| 7,034,740 B2 | 4/2006 | Witten | |
| 7,266,407 B2 * | 9/2007 | Li et al. | 600/430 |
| 7,280,863 B2 * | 10/2007 | Shachar | 600/424 |
| 2003/0184467 A1 | 10/2003 | Collins | |
| 2004/0090359 A1 | 5/2004 | McMakin | |
| 2005/0062639 A1 | 3/2005 | Biggs | |
| 2006/0183995 A1 | 8/2006 | Bond | |

OTHER PUBLICATIONS

W.C. Chew et al., "Nonlinear Diffraction Tomography: The Use of Inverse Scattering for Imaging," International Journal of Imaging Systems and Technology, Wiley and Sons, vol. 7, No. 1, Mar. 21, 1996, pp. 16-24.

William H. Weedon et al., "Step-frequency radar imaging for NDE and GPR applications," Proceedings of the SPIE—The International Society for Optical Engineering USA, vol. 2275, 1994, pp. 156-167.

J.W. Lane, Jr. et al., "Borehole Radar Tomography Using Saline Tracer Injections To Image Fluid Flow In Fractured Rock"; posted on the U.S. Geological Survey website as of Nov. 1, 2001 at usgs.gov.

International Search Report and Written Opinion of the International Searching Authority for International Application No. PCT/US07/77989, mailed Jun. 26, 2008, 11 pages.

* cited by examiner

COMPUTERIZED TOMOGRAPHY USING RADAR

CROSS-REFERENCE TO RELATED APPLICATION

This application is a continuation-in-part of U.S. application Ser. No. 11/421,013, filed May 30, 2006 and titled COMPUTERIZED TOMOGRAPHY USING RADAR, now U.S. Pat. No. 7,312,742, that claims the benefit of U.S. Provisional Application No. 60/685,658 filed May 31, 2005 titled COMPUTERIZED TOMOGRAPHY USING RADAR, both of which are incorporated by reference in their entirety. This application also claims the benefit of U.S. Provisional Application No. 60/825,065, filed on Sep. 8, 2006 and titled COMPUTERIZED TOMOGRAPHY USING RADAR, which is incorporated by reference in its entirety.

TECHNICAL FIELD

This description relates to determining the internal properties of objects.

BACKGROUND

In order to detect internal characteristics of an object, such as a piece of luggage, x-rays may be used to generate an image of the internal characteristics of the object. In particular, X-rays react differently with objects of higher density, such as a metal gun, than with objects of lower density, such as a comb. By measuring such differences, images may be generated.

SUMMARY

Radar tomography may be used instead of, or in addition to, x-ray-based inspection. Radar tomography involves the processing of wideband radar signals to characterize and image the internal structures of objects in a non-invasive manner. Such a system has a broad range of uses including transportation security and medicine. For example, in the security field, the system may be used to screen luggage for threats and contraband. In the medical field, the system may be used for diagnostic imaging.

Traditionally, these tasks have been performed by x-ray devices which provide excellent high resolution images due to the small wavelengths of the x-ray energy. While radar, with its much longer wavelengths may not achieve similar resolution, it can provide an image at far lower cost, with lower power requirements, and reduced hardware complexity.

In one general aspect, contraband is detected by receiving a location of interest relative to a target space and transmitting a radar signal in the direction of the location of interest. Deflected portions of the radar signal are detected with multiple receiving structures. The detected deflected portions are processed to generate processed data including information associated with amplitudes and phases of the detected deflected portions, and with the locations of the receiving structures at which the detected deflected portions were detected. The processed data is analyzed to determine information corresponding to dielectric properties, where the dielectric properties correspond to particular positions within the target space. A determination is made as to whether contraband is present in the target space based on the dielectric properties.

Implementations may include one or more of the following features. For example, x-ray radiation may be transmitted and detected in the target space. The location of interest relative to the target space may be determined based on the detected x-ray radiation.

A characteristic related to absorption of x-rays may be determined for a portion of the target space, and determining the location of interest may include using the characteristic related to absorption of x-rays for the portion of the target space. A determination may be made as to whether contraband is included in the target space based on the dielectric properties and the characteristic related to absorption of x-rays for the portion of the target space.

Portions of the radar signal that passed through an object corresponding to the location of interest may be detected with multiple receiving structures. The detected portions of the radar signal that passed through the object may be processed to determine information corresponding to loss properties, the loss properties corresponding to the object within the target space. A determination as to whether contraband is present in the target space may be based on the dielectric properties and the loss properties. A determination as to whether contraband is present in the target space may be made using the dielectric properties, the loss properties and the characteristic related to absorption of x-rays for the portion of the target space.

Operations may be performed conditioned upon a determination that the dielectric properties are consistent with dielectric properties of contraband where the operations include detecting, with multiple receiving structures, portions of the radar signal that passed through an object corresponding to the location of interest; processing the detected portions of the radar signal that passed through the object to determine information corresponding to loss properties, the loss properties corresponding to the object within the target space; and determining whether contraband is present in the target space based on the dielectric properties and the loss properties.

The contraband may include or be an explosive, a liquid and/or a foodstuff. The contraband may be included on or near a person, or in a container that is scanned independently of a person.

Transmitting a radar signal may include transmitting a stepped-frequency radar signal and/or a swept-frequency radar signal. An x-ray device may be configured to send the location of interest within the target space to the radar tomography device.

In another general aspect, a location of interest relative to a target space is received, and a radar signal is transmitted in the direction of the location of interest. Portions of the radar signal are detected with multiple receiving structures. The detected portions are processed to generate information corresponding to dielectric or loss properties, the properties corresponding to particular positions within the target space. A determination is made as to whether contraband is present in the target space based on the determined properties.

Implementations may include one or more of the features noted above.

In yet another general aspect, an image of living tissue is generated by transmitting a radar signal through living tissue. Deflected portions of the radar signal are detected with multiple receiving structures. The detected deflected portions are processed to generate processed data including information associated with amplitudes and phases of the detected deflected portions, and with the locations of the receiving structures at which the detected deflected portions were detected. The processed data is analyzed to determine information corresponding to dielectric properties, where the dielectric properties correspond to particular positions of the living tissue. An image of the living tissue is generated based on the dielectric properties of the living tissue.

Implementations may include one or more of the following features. For example, an anomalous portion of living tissue may be detected based on the dielectric properties of the living tissue. An anomalous portion of living tissue may be detected based on a difference of dielectric properties of a portion the living tissue from the dielectric properties of another portion of the living tissue. The anomalous portion of living tissue may include or be a tumor or a precancerous growth.

Implementations of the techniques discussed above may include a method or process, a system or apparatus, or computer software on a computer-accessible medium.

The details of one or more implementations are set forth in the accompanying drawings and the description below. Other features will be apparent from the description and drawings, and from the claims.

DESCRIPTION OF DRAWINGS

Like reference symbols in the various drawings indicate like elements.

DETAILED DESCRIPTION

Figure 1:
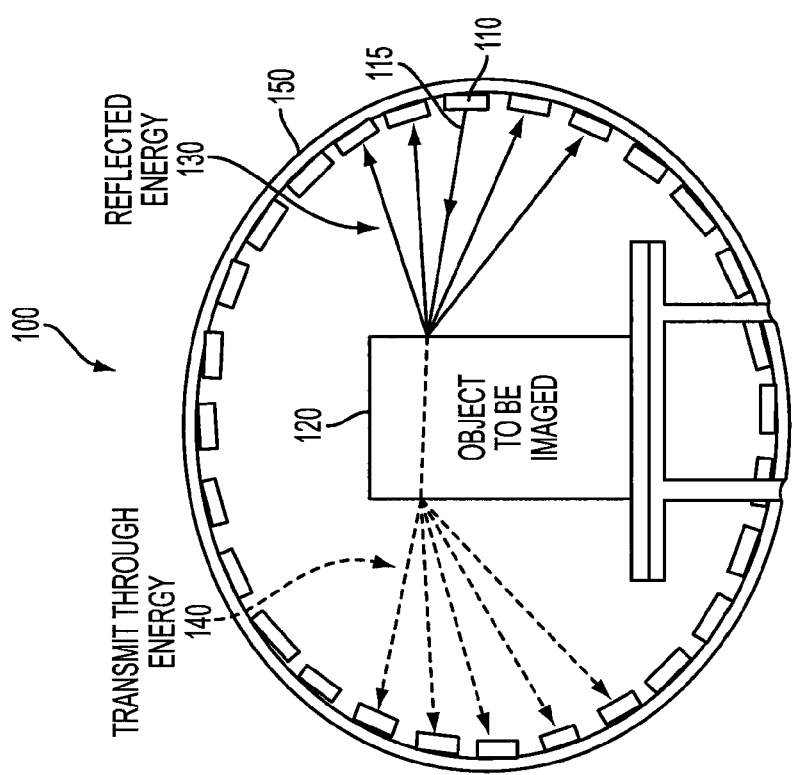
FIG. 1 illustrates a cross section of a device for scanning objects using computerized radar tomography.

To map internal characteristics of an object, a radar signal may be transmitted through the object, which deflects portions of the signal. The deflected portions of the signal and/or the portions of the signal that pass through the object may be analyzed using computerized tomography to reveal internal characteristics of the object. In particular, a radar signal striking an object will be deflected based on the dielectric properties of the object. A signal deflected by a low dielectric material will exhibit lower signal strength (i.e., signal amplitude) than a signal deflected by a high dielectric material. A radar signal loses strength or attenuates as the signal passes through an object.

In various implementations, a series of receiving antennas are arranged to form a circumference around an object to be detected. A signal is transmitted towards an object, and the receiving antennas detect deflected portions of the signal. The detected portions of the signal received by the different receiving antennas are processed, with the processing taking into account the amplitude and phase of a detected signal, the position of the associated receiving antenna, and the position of the transmitting antenna that generated the signal. The amplitude is indicative of dielectric properties at a point location that reflected the signal, and the phase and the positions of the transmitting and receiving antennas are indicative of the location in space of the point location. By analyzing the information associated with amplitude, phase, and position of the receiving antenna, a dielectric level may be determined for a point in space. The portions of the signal that pass through the object also may be received by receiving antennas. The attenuation of the signal as it passes through the object may be used to help identify internal characteristics of the object. For example, the amount of attenuation of the signal that has passed through an object is based on the material composition of the object. The attenuation caused by a material may be referred to as the loss property of the material.

Computerized tomography may be carried out by determining data for a number of point locations (e.g., pixels) of an object and combining the point locations to form a two-dimensional representation (e.g., a map) corresponding to the dielectric level of the object. Successive two-dimensional representations may be combined to form a three-dimensional representation, or a three-dimensional representation may be formed directly.

The above process may be used to scan luggage including multiple grouped non-metallic and metallic objects to detect weapons or explosives that might otherwise not be detected. For example, while objects with substantially different densities, such as a knife and a comb, may be easily detected using X-ray scanning, objects of similar density, such as a salami and a plastic explosive, may be missed. Since many objects with similar densities have substantially different dielectric properties, computerized radar tomography may be used to identify and distinguish their presence. In another example, because objects with similar dielectric properties may have different loss properties, the loss property may be used to identify and distinguish different objects that have similar dielectric properties.

Referring to FIG. 1, a system 100 for scanning objects using computerized radar tomography includes a series of elements that form a circumference 150 surrounding an object 120. A particular element may be a transmit element configured to transmit a radar signal, a receive element configured to receive a deflected radar signal, or a transceive element configured to transmit and receive a radar signal. In certain implementations, each of the elements is a transceive element that may both transmit and receive radar signals.

In the system 100, a transmit element 110 emits a stepped frequency radar signal 115 in the direction of an object 120. Based on the dielectric properties of the object 120, part of the signal is deflected. The deflected signal 130 may be detected by multiple receive elements located along the circumference of elements 150. Parts 140 of the signal may transmit through the object 120 and be detected by multiple other receive elements. For a detected signal, information associated with the phase and amplitude of the signal, as well as the location of the element that received the signal, is processed. The processed information is analyzed to determine data associated with a dielectric level at a series of point locations which may be used to generate an image.

A single frequency or multiple frequencies may be transmitted concurrently. Also, a single element or multiple elements may detect the signal concurrently. The amount of overlap in frequency transmission or signal detection may be adjusted order to control the speed of the process and the complexity of the device design.

In one implementation, an element transmits a single frequency in the stepped-frequency radar signal that may be detected, sequentially, by a series of receive element over a period of time. In other words, a single element detects a signal corresponding to the frequency for a short period, then another receive element detects the signal corresponding to the frequency, then this process continues until all receive elements have "listened" for signals at the given frequency. The frequency then is transmitted by another element, and may also be detected, sequentially, by receive elements for a period of time. The process continues until all transmit elements around the circumference have transmitted the frequency and the transmitted frequency has been "listened" to by all receive elements. Next, another frequency in the stepped-frequency radar signal is transmitted and the process repeats until all frequencies have been transmitted and received.

In particular implementations, to increase the speed of the process, two or more of the receive elements concurrently detect a transmitted signal of a particular frequency that is transmitted by a transmit element. The receive elements that concurrently detect a signal may include all of the receive elements or a subset of the receive elements. In one implementation, there is a sequence of subsets that each detects for a period until all receive elements have "listened." This process enables detection by all of the receive elements within a shorter period of time. The same frequency is then transmitted by another element, and this frequency may also be detected concurrently by all receive elements or by a subset of receive elements. Next, another frequency, or set of frequencies, is transmitted and the process repeats. In one implementation, multiple transmit elements concurrently transmit differing frequencies of a signal and the two or more receive elements concurrently detect the transmitted signal.

After determining data for a series of point locations, a two dimensional image that represents a cross-section of the object may be generated. The object, or the elements, may be adjusted, and another set of data for a series of point locations may be generated, or multiple scans from multiple rings of elements may be operated concurrently. Using this process, a series of two dimensional image slices may be combined to form a three dimensional image of an object and its internal dielectric characteristics. A three-dimensional image may be formed directly such that two-dimensional images need not be combined to form a three-dimensional image. A two-dimensional or three-dimensional image of a scanned piece of luggage may show a plastic explosive contrasted with an adjacent inert object of similar density.

The system 100 may be used for generating images of living tissue. For example, the object 120 may be a piece of tissue that is being scanned to detect areas with increased blood-flow, such as tumors or precancerous growths. The system 100 may be particularly useful in scanning areas that are relatively close to the surface of the skin, where a greater dichotomy between water content in an area and adjacent tissue may be present.

The previous description is an example system, and other systems may be organized differently. For example, the elements need not form a circumference around the object, and may form other shapes that are two or three dimensional.

Figure 2:
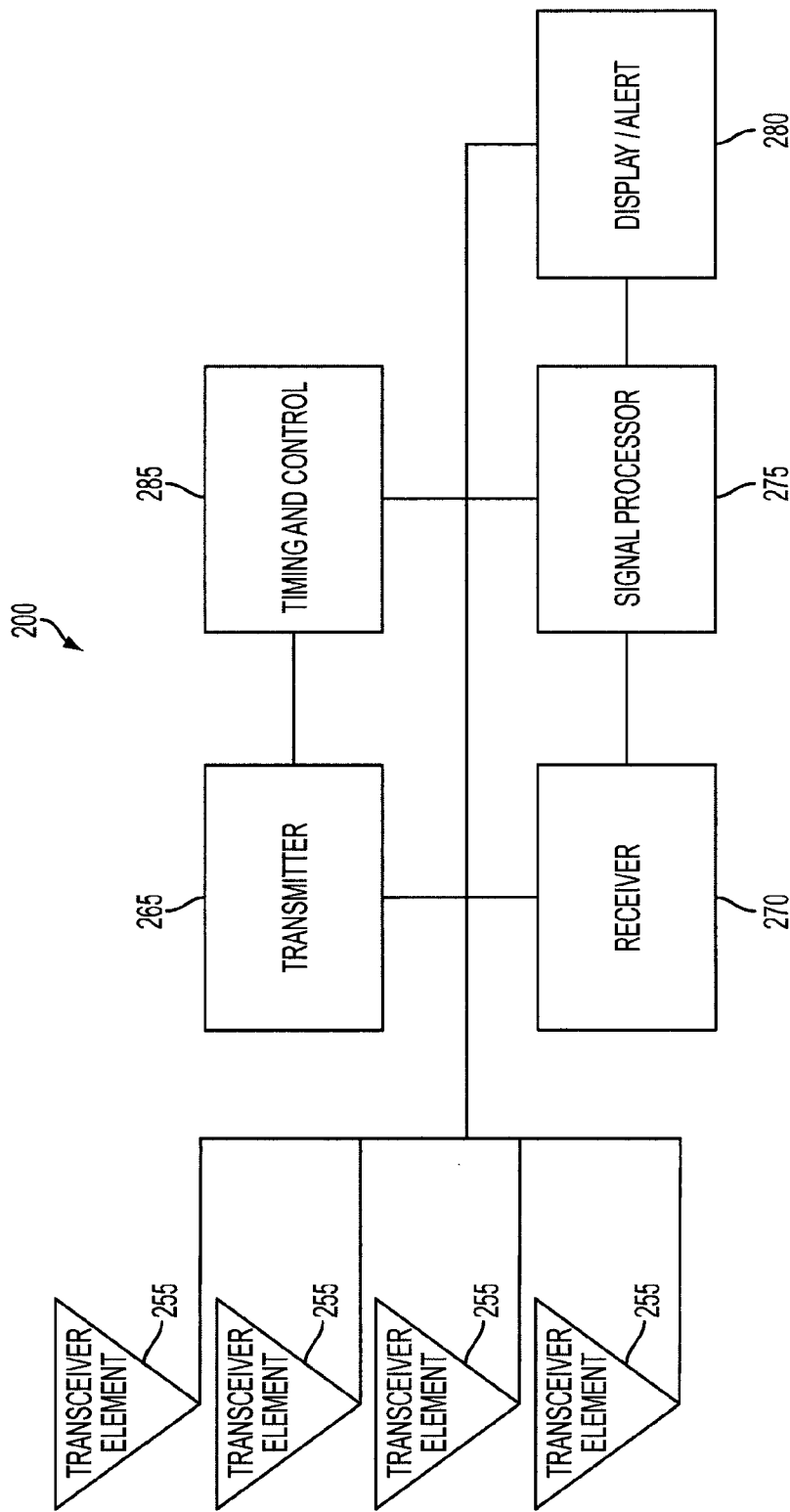
FIG. 2 is a block diagram of a computerized radar tomography system.

Referring to FIG. 2, a system 200, such as a stepped-frequency radar scanner, includes transceiver elements for transmitting and receiving a stepped-frequency radar signal to analyze objects. The system 200 is shown as a series of transceive elements 255 connected to a radar transmitter 265 and a radar receiver 270. As shown, the system 200 may be particularly well suited to transmit from a transceiver element 255 operating as a transmit element, and to concurrently receive from a single transceiver element operating as a receive element. Other implementations may have multiple radar transmitters 265 or radar receivers 270 to facilitate concurrent transmission and receiving from multiple transceiver elements. In one implementation, the transceive elements 255 are replaced with separate transmit and receive elements.

The transceive elements 255 may be connected to a radar transmitter 265 that generates an RF signal to be transmitted toward an object to be analyzed. The RF signal includes frequencies that cover a bandwidth in increments of frequency steps. For example, the signal may include a nominal frequency operating with a center frequency in the UHF, L, S or X bands.

The transceive elements 255 may be connected to a radar receiver 270 that receives the deflected RF signals from the object. The radar receiver 270 may filter or convert the received signals to signal data in a usable format, and is coupled to a signal processing system 275 that processes the data. The signal processing system 275 is coupled to a display 280 and a timing and control module 285. The display 280 may provide an audible and/or a visual alert when an object is detected by the scanner, or may generate two-dimensional or three-dimensional images of the scanned object. The timing and control module 285 may be connected to the transceive elements 255, the radar transmitter 265, the radar receiver 270, the signal processor 275, and the display 280. The timing and control module 285 may provide signals, such as a clock signal and control signals, to the other components of the system 200. In various implementations, the timing and control module 285 uses switches to sequentially couple the radar transmitter 265 and the radar receiver 270 to an appropriate transceive element in order to scan the object.

Implementations may employ scanning processes that combine computerized tomography of radar signals ("CTR") with computerized tomography of x-rays (CTX). In particular, a sequential or concurrent transmission of x-rays may be used to scan other characteristics of the object. In one implementation, a scan using CTX is conducted, and the results may trigger a scan using CTR. For example, a scan using CTX may show an area that is not easily characterized, such as a dark area in a piece of luggage (e.g., scan results of a metal container in the luggage). The signal processor 275 may automatically recognize the deficiency of the scan using CTX and initiate a scan of the area using CTR. In another implementation, the order of the process is reversed, and the scan using CTR is conducted first and may result in a scan using CTX. Differing characteristics of objects to be scanned, or differing characteristics to be searched for while scanning, may make one method more productive than the other.

Particular implementations may employ phase or amplitude corrections of the received signal. The location of the point to be scanned, the location of the transmit or receive elements, the electrical and physical properties of system 200, or the dielectric properties of the object may all introduce errors or distortions into the signal that may lower precision of generated data. The receiver 270 or processor 275 may automatically correct the phase or amplitude of the received signal based on known properties, such as element location or other properties of system 200.

In particular, differing dielectric properties within an object may introduce an error in the deflected signal. This error may be similar to the effect of shining a light through mediums of multiple densities, such as, for example, the distortion produced by observing light that transmits through the glass and water of an aquarium. If known, the error may be corrected using the dielectric properties of the object. If not known, the dielectric properties of an object may be estimated by scanning and using iterative calculations.

The previous description is an example implementation, and other system may be organized differently. For example, the receiver 270 and the transmitter 265 may be organized together.

Figure 3:
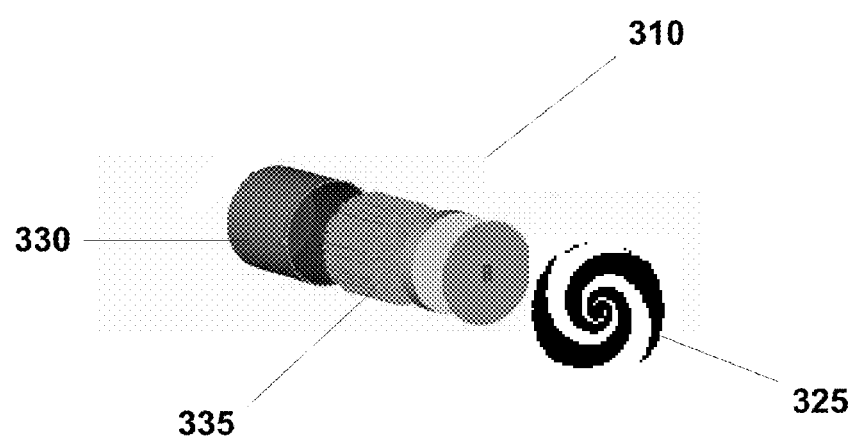
FIG. 3 illustrates an antenna design.

FIG. 3 illustrates aspects of an element design 300 that may be used in various implementations of the device of FIG. 1. The design 300 includes a transmit element 310, and, in some implementations, may include a receive element or a transceive element. As shown, the design 300 employs a spiral antenna 325 that supports a wide bandwidth. The input impedance and the radiation patterns will vary little over the frequency range used. The spiral element 325 may be constructed by etching a spiral pattern on a printed circuit board. A planar, printed circuit, spiral element radiates perpendicularly to the plane of the spiral. The spiral 325 is located at the end of a cylindrical metal cavity 330 (the cavity back) to provide isolation from neighboring elements and electronics. Typically, an absorber 335 is used on the top side of the spiral inside the cavity 330 to make sure the element responds only in one direction.

The previous description provides an exemplary implementation of an element design. Other implementations may include different features, such as an endfire waveguide antenna. Such a configuration may be slightly larger than the spiral configuration. The endfire waveguide antenna reduces the signal spot size, thus making the exact position at which the signal is reflected easier to locate. Other suitable types of wideband elements may also be used.

Figure 4:
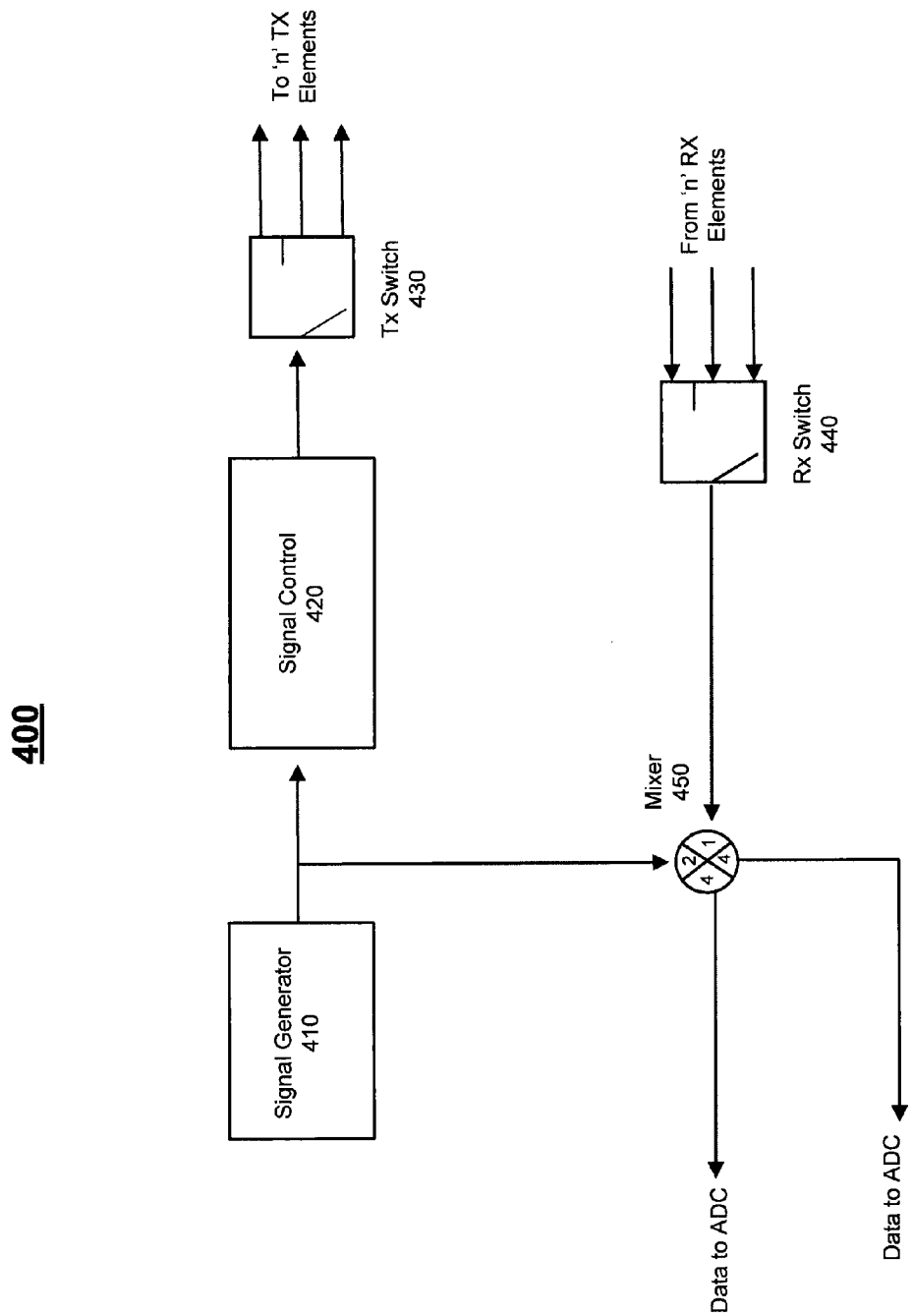
FIG. 4 is a block diagram of a system to transmit and receive a radar signal.

Referring to FIG. 4, an exemplary system 400 to transmit and receive a radar signal includes a signal generator 410, a signal control 420, a transmit switch connecting 'n' transmit or transceive elements 430, a receive switch connecting 'n' receive or transceive elements 440, and a mixer 450, which may be in the form of a quadrature demodulator.

The conversion system 400 may be used in the system 200. In this case, the signal generator 410 may be included in the transmitter 265, the signal control 420 and the switches 430 and 440 may be included in timing and control 285, and the mixer 450 may be included in the receiver 270.

In the system 400, a transmission signal is generated and transmitted through a transmit element. Reflected portions of the transmitted signal are received through a receive element, which may optionally be the same element as the transmit element. The transmitted signal and the generated signal are input to the mixer 450, which outputs an in-phase signal and an out-of-phase (quadrature) signal.

The signal generator 410 generates a signal to be broadcast by the antenna. The signal generator 410 may include a phase lock loop synchronized to a crystal oscillator. The signal generated by the signal generator 410 is input to a mixer 450 and to a signal control 420. The signal control 420 may amplify or otherwise condition the signal to enable transmission by the transmit element. The signal control 420 provides the signal to a transmit element through the transmit switch 430. The transmit switch 430 enables the signal generator 410 to transmit the signal using one or more transmit elements out of 'n' transmit elements. The receive switch 440 enables one or more receive elements out of 'n' receive elements to send a received signal to the mixer 450. The transmit and receive switches 430 and 440 may include, for example, single pole double throw (SPDT) switches and/or a computerized control system. In one implementation, all elements are transceive elements, and a single switching system replaces the transmit and receive switches 430 and 440.

The transmit element emits the controlled signal and strikes objects in the environment. Portions of the transmitted signal may be reflected. The reflected portions, which may exhibit any of an amplitude, frequency, or phase shift, are received by the receive element. The receive element inputs the received signal to a receive switch 440 that enables connection of the signal to the mixer 450.

Some implementations may use other mechanisms, such as a control system, in place of the transmit switch 430 and the receive switch 440. In one implementation, the receive element is input directly to a mixer without a switch.

The mixer 450 receives the signal from the signal generator 410 in an input. In another input, either the transmission signal or the received signal may be received by the mixer 450, based upon the transmit switch 430 and the receive switch 440. The mixer 450 converts input signals to a form that is more easily processed, such as, for example, an in-phase and an out of phase component at a baseband frequency. Various implementations do not directly input the signal generator 410 to the mixer 450.

As shown, the mixer 450 is a quadrature demodulator, though other signal conversion systems may be used. The quadrature demodulator outputs "I" and "Q" data (referred to as IQ data). The output signals may be analyzed, to determine any of an amplitude, frequency, or phase shift between transmitted and received signals that may be indicative of dielectric characteristics of an object. In some implementations, separate IQ data may be generated for each transmitted frequency.

The previous description is an example implementation of the transmit and receive system. Other implementations may include different components. For example, in various implementations, multiple mixers or other components may be included to facilitate transmission or receiving of multiple frequencies, and/or by multiple element, concurrently.

Figure 5:
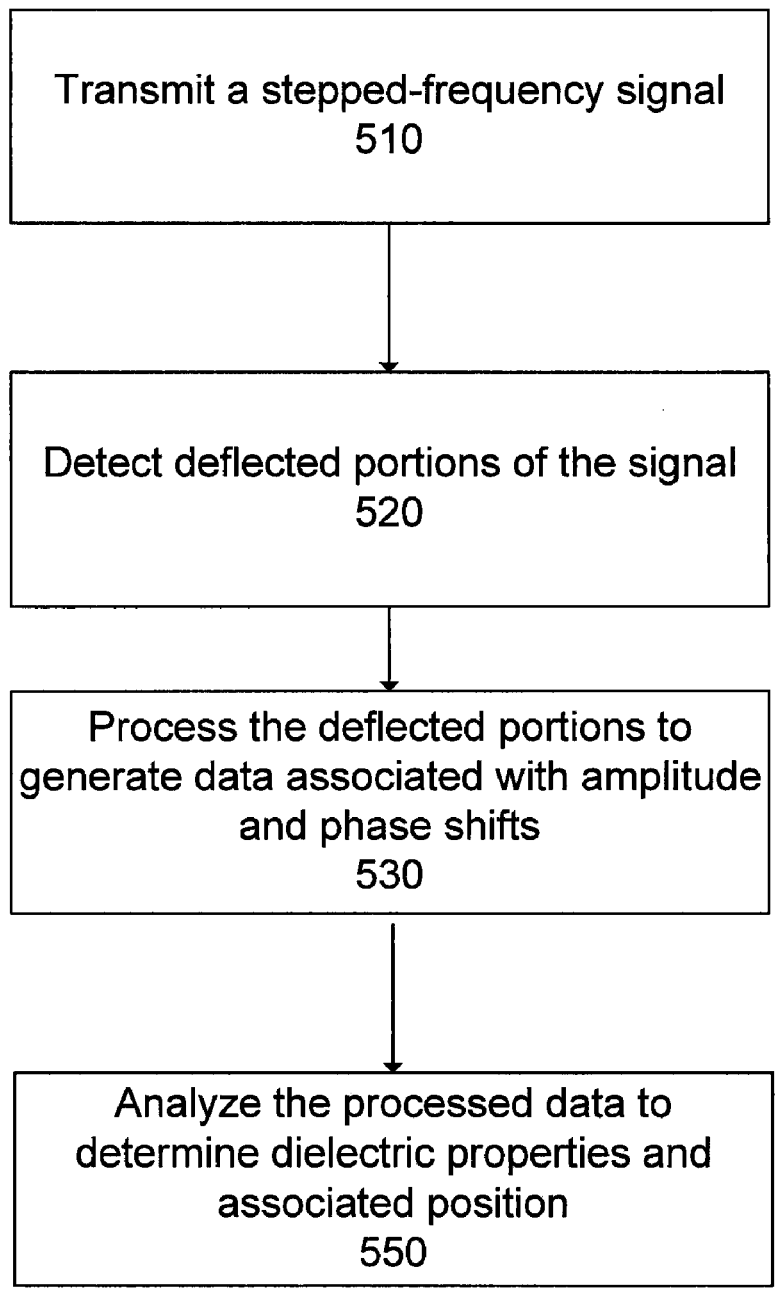
FIG. 5 is a flow chart of a process using computerized radar tomography to scan objects.

FIG. 5 shows a process 500 to scan objects using CTR. The process 500 may be implemented on the system 100 of FIG. 1 or another system. The process 500 begins when a stepped-frequency signal is transmitted by an element (510). The stepped-frequency radar signal may be a radar signal including multiple frequencies and phases that are transmitted concurrently or consecutively. The radar may change frequencies in steps or continuously. In one implementation, each transmission cycles through a frequency bandwidth that includes multiple transmitted frequencies that are separated by frequency steps. In the implementation, while cycling through the bandwidth, each frequency is transmitted for a period of time, followed by the next frequency, until the bandwidth has been crossed. In another implementation, the signal frequency is swept from a low frequency to a higher frequency, with frequencies between the low and high frequency being transmitted. Although multiple frequencies may be sent, one after another, the transmitted and received signals are discussed as a single signal to simplify discussion. After transmission, the signal strikes an object and may be deflected based on the dielectric characteristics of the object.

One or more elements detect deflected portions of the signal (520). The elements may be arranged along a line, curve, circumference, or other shape. The detected signal includes an amplitude, phase, and/or frequency that may have been altered by the object. For example, the amplitude may be affected by the dielectric properties of the object, the phase may be affected by the position of the object, and the frequency may be shifted by movement of the object.

Deflected portions of the signal are processed (530). The processing may identify, for example, information associated with the amplitude and phase of the signal, and the receiving structure in which the deflected portion was detected. The processing may include a correction step to calibrate the data or processing steps based on electrical or physical properties of the device or receiving structure, or based on estimated or actual dielectric properties of the object. The processing may include combining the measurements from some or all of the detected signals. Implementations may adjust for the path lengths and delays due to the material propagation times, and adjust for magnitude changes due to the attenuation of the signals in the different materials. The adjustments for the path lengths may include a phase correction of the signal. The adjustments for the material propagation time and attenuation may include a phase and magnitude correction.

In particular implementations, processing of the deflected portions (530) includes identifying information associated with a frequency shift. The object may be moved to induce a Doppler shift that is used to separate detected signals that are deflected by the object from detected signals that are reflected by other system components or noise signals. For example, if an object is known to be moving, detected signals that do not exhibit a Doppler shift may be discarded. In one implementations, a vibrating platform is used to induce vibrations in the object. In another implementation, a moving conveyer belt is used to induce movement.

The processed data is analyzed to determine information corresponding to dielectric properties of the a particular position within the object (550). This analysis may include, for example, Fourier transforms for multiple integration times, or other processing techniques.

The process 500 is an example implementation of a process to sense characteristics of an object using a stepped-frequency sensor device. Other implementations may include additional or different steps. For example, processing and analyzing the data (530 and 550) may be conducted in a single step. In another example, signals that pass through the object are detected and characteristics of the object may be determined based on the amount of attenuation of the signal.

Figure 6:
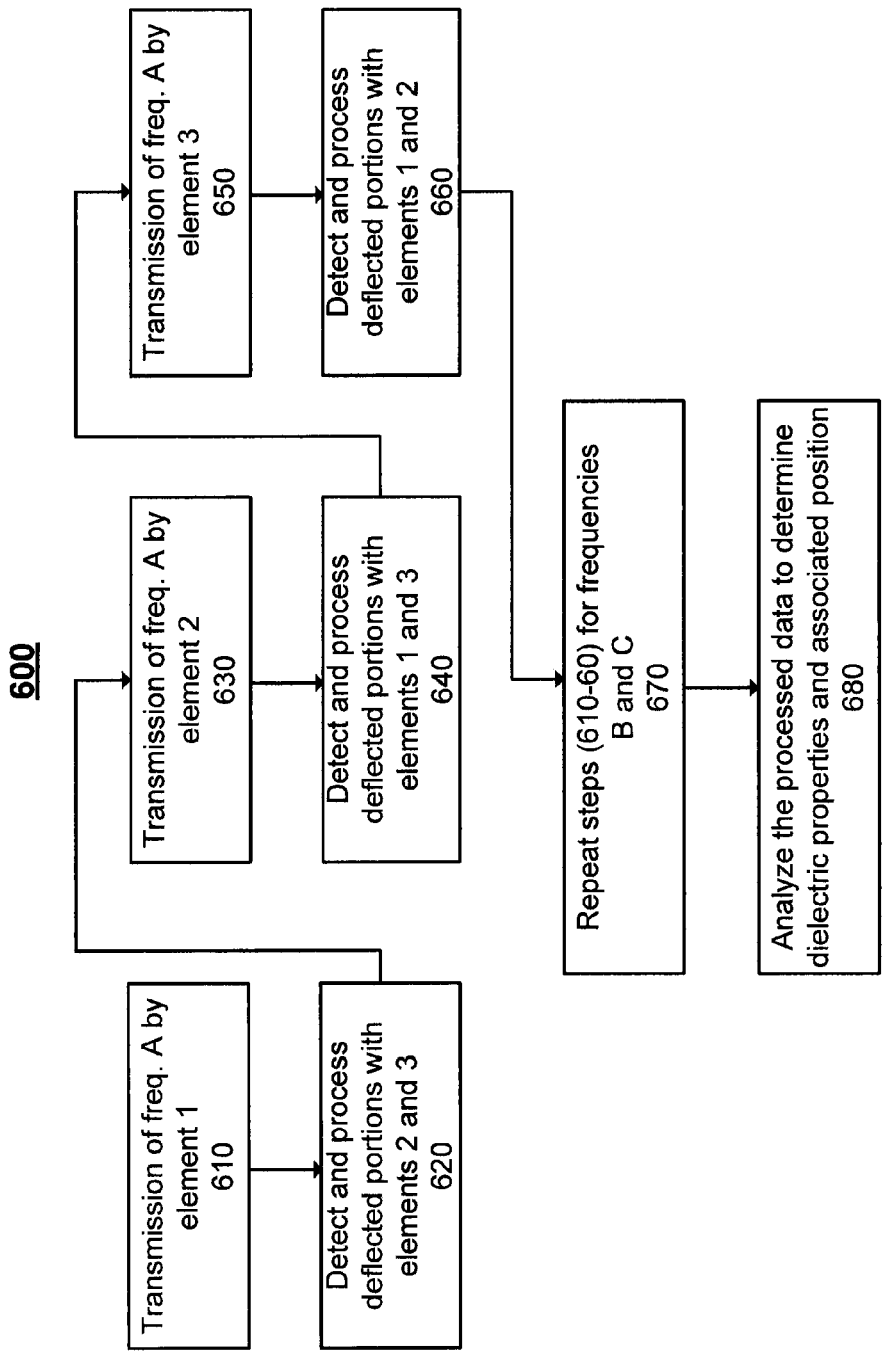
FIG. 6 is a flow chart of a process using computerized radar tomography to scan objects with multiple receive elements.

FIG. 6 shows a process 600 to scan objects using CRT with multiple receive elements. The process 600 may be implemented on the system 100 of FIG. 1 or another system. FIG. 6 is included to illustrate an exemplary process in which sequential scanning is conducted across multiple elements and multiple frequencies. In the process 600, three transceive elements that each may operate as a transmit or receive element are included. The stepped-frequency radar signal consists of three frequencies, A, B, and C, to be transmitted.

The process 600 begins when a stepped-frequency signal at frequency A is transmitted by element 1 operating as a transmit element (610). Elements 2 and 3 operate as receiving elements to detect deflected portions of the signal transmitted by element 1. The detected portions are processed to generate data associated with amplitude and phase shifts (620). Elements 2 and 3 may detect the deflected portions sequentially or concurrently.

Next, element 2 operates as a transmit element to transmit the stepped-frequency signal at frequency A (630). Elements 1 and 3 operate as receiving elements to detect deflected portions of the signal transmitted by element 2. The detected portions are processed to generate data associated with amplitude and phase shifts (640).

Then, element 3 operates as a transmit element to transmit the stepped-frequency signal at frequency A (650). Elements 1 and 2 operate as receiving elements to detect deflected portions of the signal transmitted by element 3. The detected portions are processed to generate data associated with amplitude and phase shifts (660).

Next, the process (steps 610-660) repeats for the second frequency, B, and then for the third frequency, C (step 670). Finally, the processed data is analyzed to determine dielectric properties and the associated position of the dielectric properties within the object (680).

Some implementations may include additional or alternative steps. For example, the processing of detected signal portions need not be conducted as the detection occurs. In various implementations, the processing occurs after transmission of all frequencies.

Figure 7:
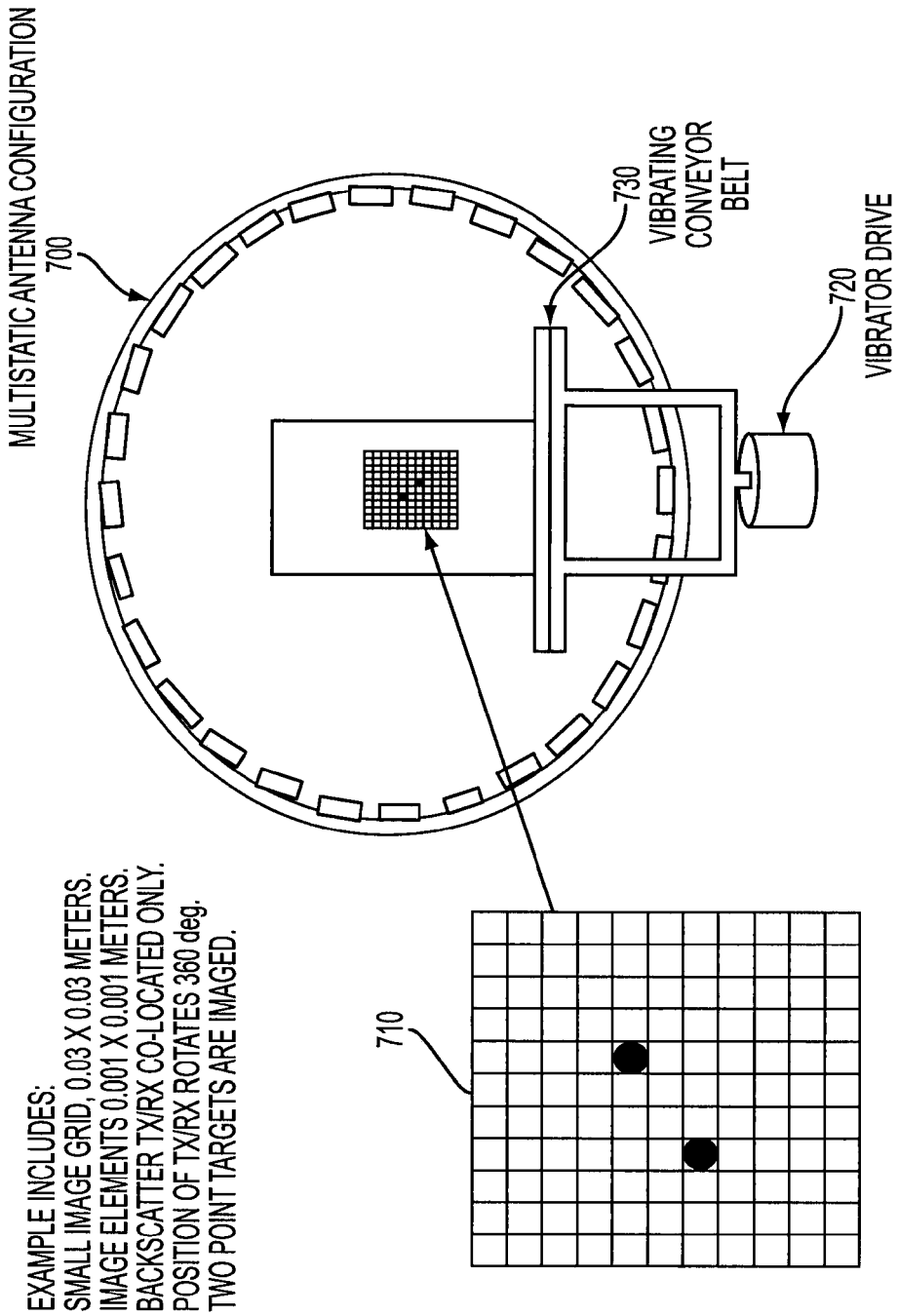
FIGS. 7 and 8 illustrate an implementation of a device to scan objects using computerized radar tomography and data associated with a scan.
Figure 8:
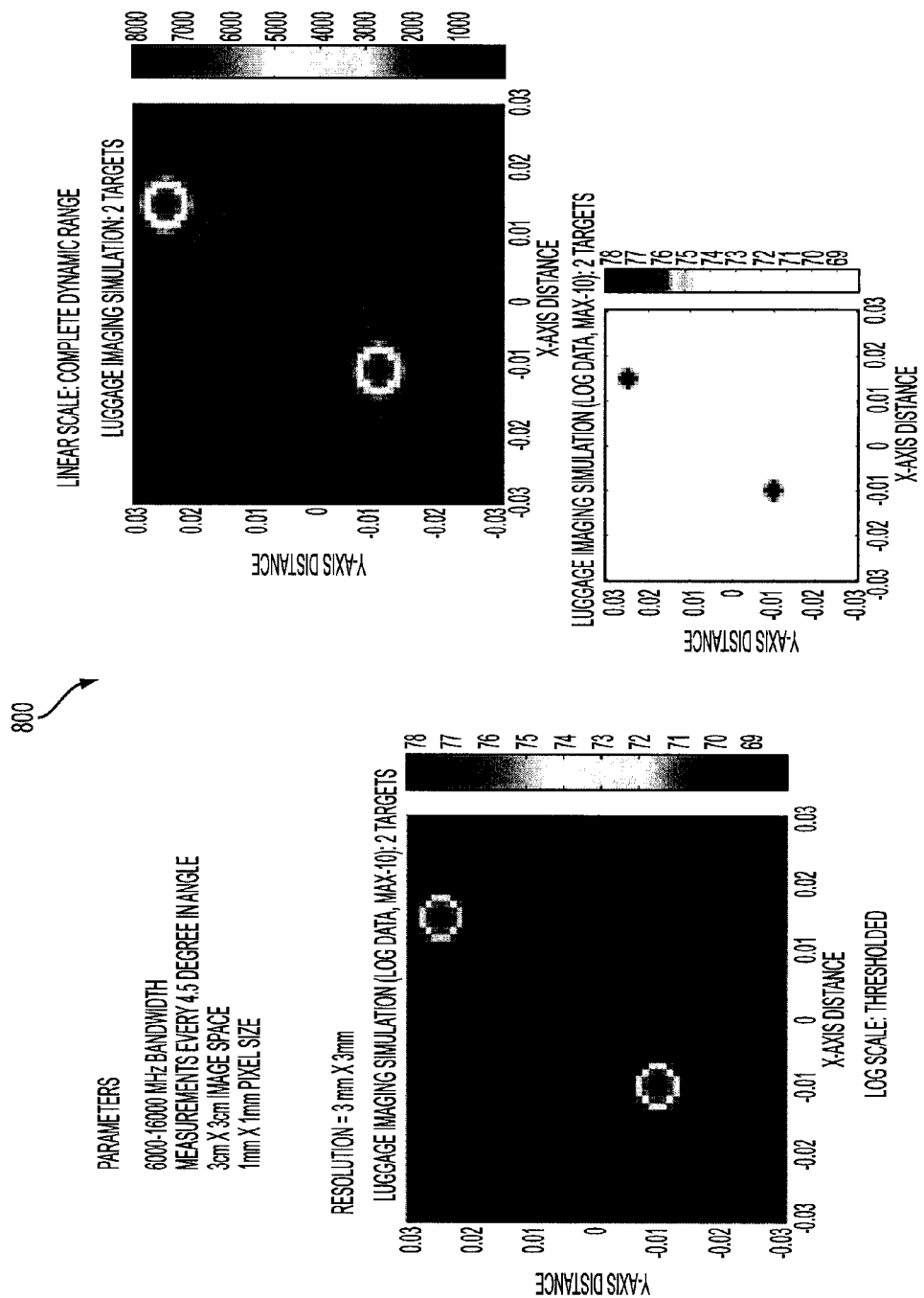

Referring to FIG. 7, an example implementation of a device 700 to scan objects using computerized radar tomography is shown. In the device 700, an object is positioned to be scanned. The object includes two areas that include dielectric properties different from the surrounding dielectric properties in the object. The device 700 includes a vibrating drive 720 and a vibrating conveyer belt to induce movement in the object. Due to the induced movement, portions of the radar signal deflected from the object may exhibit a Doppler shift. The Doppler shift may be used to distinguish detected signals that were actually deflected by the object from noise and detected signals that were deflected by other objects (e.g., system components). FIG. 8 shows an example of results 800 of analyzed data. In the results, the dielectric level is shown as a function of position.

Figure 9:
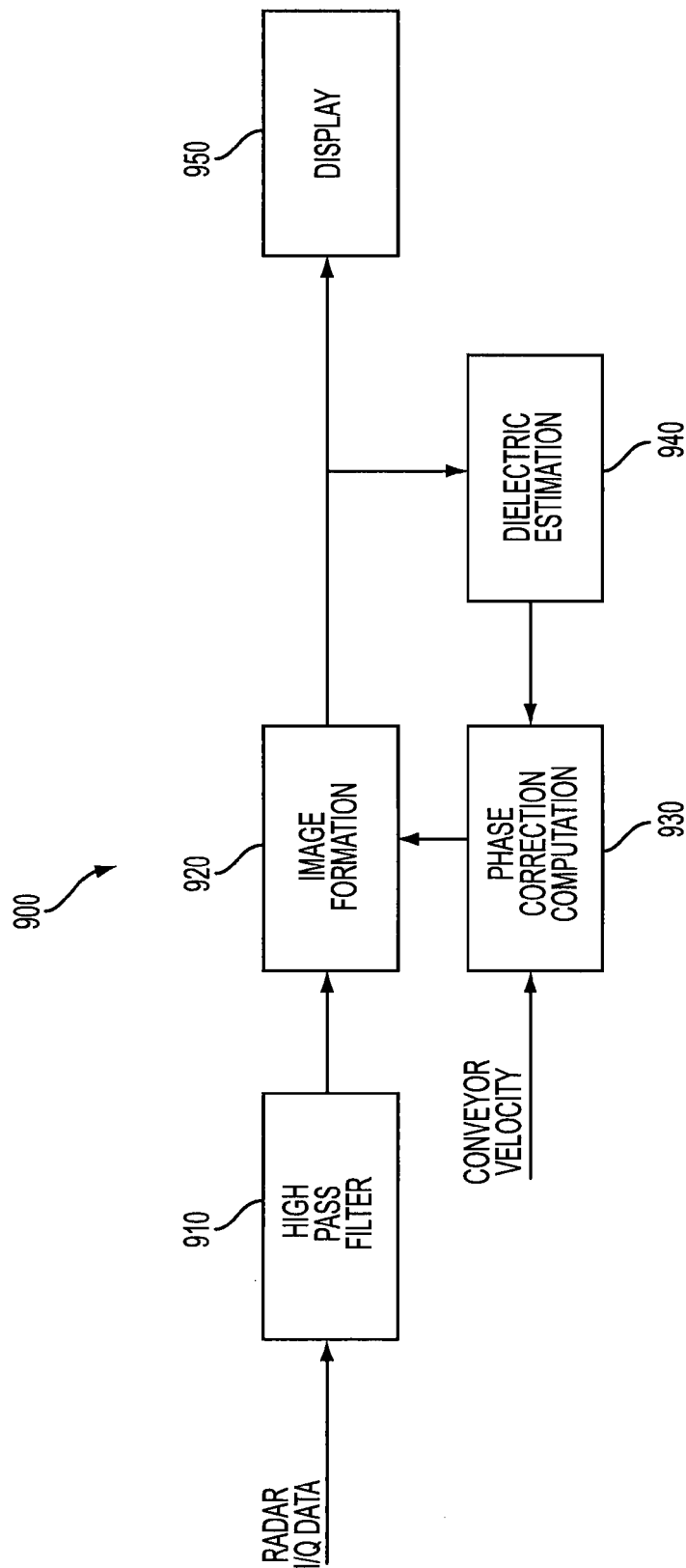
FIG. 9 is a block diagram of a system to process and analyze signal data.

Referring to FIG. 9, an exemplary system 900 to process and analyze signal data includes a high pass filter 910, an image formation unit 920, a phase correction computation unit 930, a dielectric estimation unit 940, and a display 950. The system 900 is an example of a system for processing and analyzing signal data generated from an object that is moved using a moving conveyer belt.

The output of the radar receiver is in the form of digitized in-phase (I) and quadrature (Q) time samples of the data received by each antenna at each frequency. The output may, for example, be the output of the mixer 450 of FIG. 4. For a system with N antennas and M frequencies, there will be N times M I/Q pair of digital samples collected for one complete revolution around the antenna array, that provides one "look" at the object. Additionally, as the objects moves along the conveyor belt, a broad antenna element transmission field-width (beamwidth) increases visibility of the object both prior to and after passing through the plane of the array, providing multiple "looks" at any given point in the object. The number of available looks, K, is directly proportional to the product of the beamwidth, range to object, conveyor belt rate, and "look" rate. The K "looks" constitute one "dwell" on the object and is comprised of I/Q pairs of digital samples in a quantity of N times M times K.

The samples from each antenna and each frequency are first processed through a digital high-pass filter 910 to reduce interference from the leakage of the transmit signal into the receiver.

The image formation unit 920 performs computation and application of phase corrections to the I/Q data from each dwell followed by summation to affect coherent integration gain and focusing to a grid of points in the plane of the antenna array. The result is a single cross-sectional slice of the object for each dwell. Concatenation of successive slices results in a 3-dimensional image of the object.

The phase corrections computation unit 930 accounts for the change in distance between each grid location being imaged and each receive antenna as the grid of points pass through the antenna array. Using vector notation, the corrections are determined for all samples in a dwell as follows:

$$\varphi_{i,n,m,k} = \frac{2\pi}{\lambda_m} |\vec{P}_{i,k} - \vec{A}_n|$$

where:
- $\varphi_{i,n,m,k}$ is the phase correction in radians for the $i^{th}$ grid location and a sample from the $n^{th}$ antenna, $m^{th}$ frequency, and $k^{th}$ dwell,
- $\lambda_m$ is the wavelength corresponding to the $m^{th}$ frequency,
- $\vec{P}_{i,k}$ is the 3-dimensional position vector to the $i^{th}$ grid position at the $k^{th}$ dwell, and
- $\vec{A}_n$ is the 3-dimensional position vector to the $n^{th}$ antenna.

Amplitude and phase data for each image grid location are used to estimate dielectric properties 940 and adjust the effective wavelength used in the phase correction computation. This is performed iteratively until the image is fully focused. The resulting image is shown on the display 950.

Figure 10:
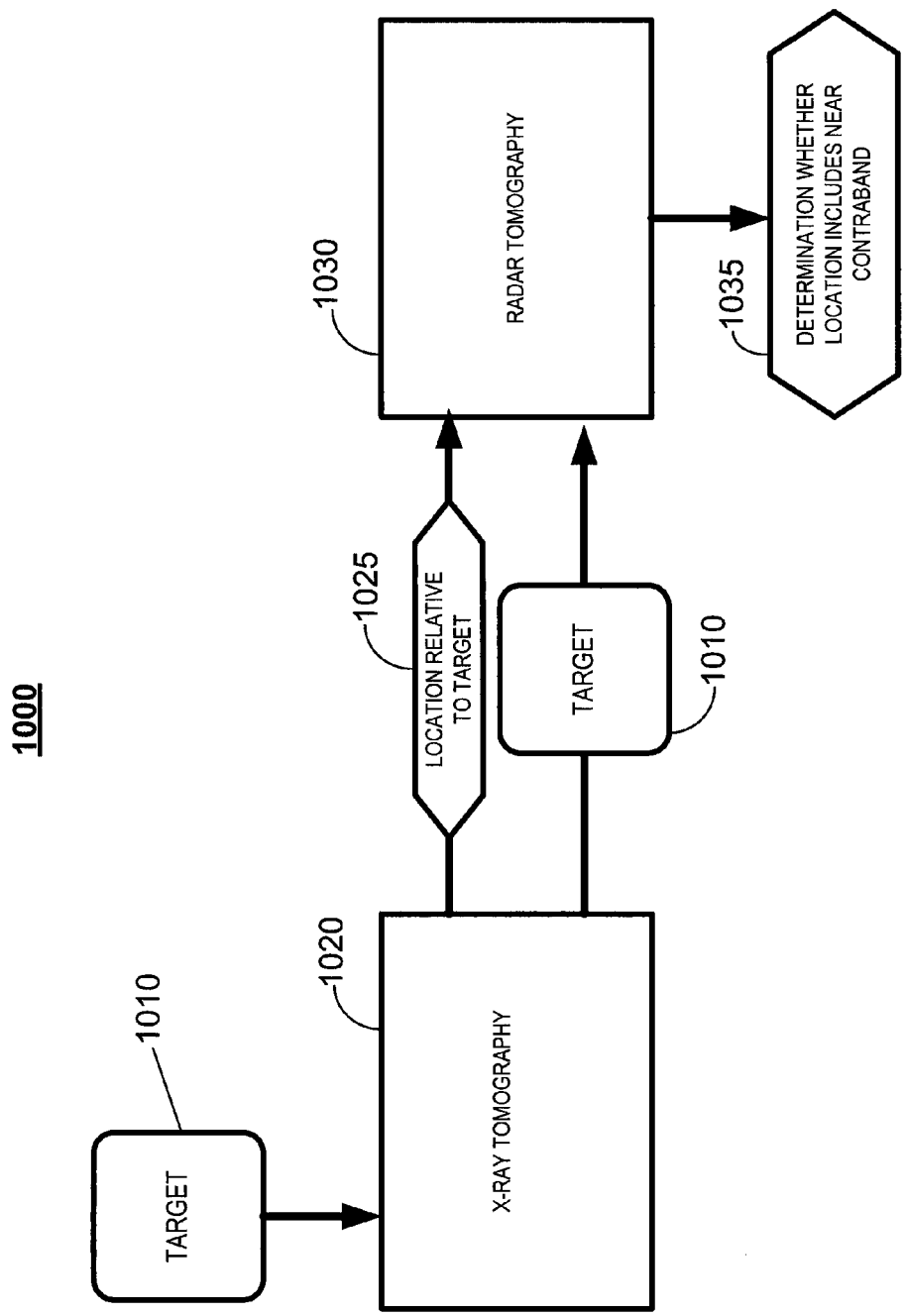
FIGS. 10, 12A and 12B depict processes using x-ray tomography and computerized radar tomography to detect contraband.
Figure 11:
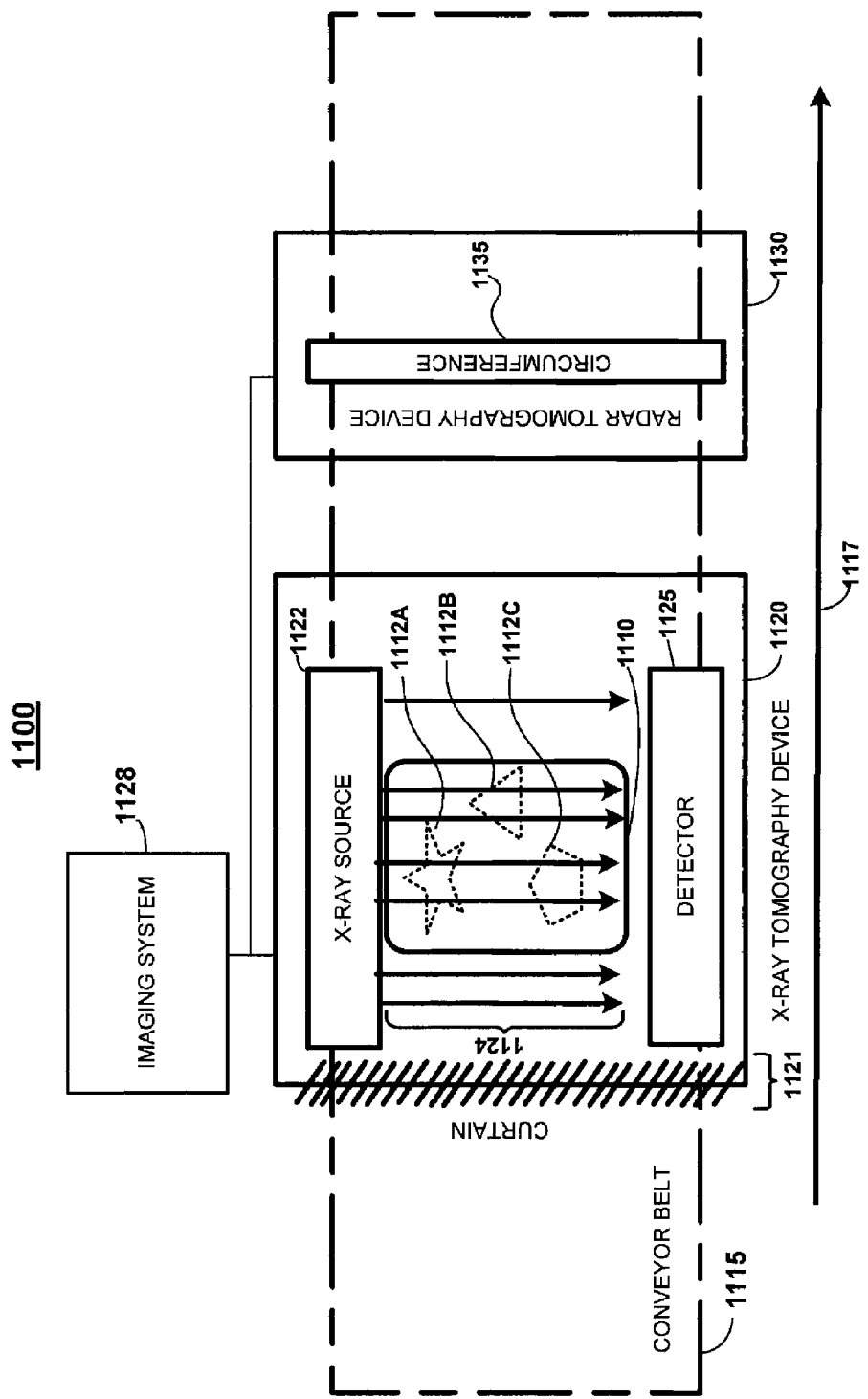
FIG. 11 illustrates a plan view of a system capable of using x-ray tomography and computerized radar tomography to detect contraband.

FIGS. 10-12 describe various exemplary implementations of scanning processes that combine computerized tomography of radar signals with computerized tomography of x-rays. The illustrated scanning processes in FIGS. 10-12 may be used to identify contraband.

FIG. 10 depicts an exemplary process 1000 for detecting contraband or hazardous items (collectively, "contraband") that sequentially scans a target both using x-rays and radar signals. Generally, in the example process 1000, a target 1010 to be scanned for contraband is scanned using x-rays 1020 and using radar tomography 1030 to make a determination 1035 as to whether the target includes or is near contraband. In one example, the target to be scanned may be an object, such as luggage, or another type of carrier or container, to be carried on by a person or transported as cargo by commercial aircraft. In another example, the target may be a person to be scanned at a security checkpoint. Contraband may include explosives or another type of prohibited substance. The techniques and concepts, however, are not limited to airport security screening of people and baggage.

The use of x-ray images with radar tomography images may be useful, for example, in analyzing different physical properties that can be measured by x-ray images and radar tomography images. X-ray images may be used to determine atomic density and/or atomic weight ("Z") of an area within the x-ray, which helps to identify the location of an object relative to the area that was imaged. Atomic density and/or atomic weight may be used to help identify objects that may include contraband. Radar tomography may be used to determine dielectric and/or loss properties of an area or object that is imaged The use of multiple different properties, such as by employing both x-ray imaging and radar tomography, may help improve the accuracy and reduce false positive results of security scanning (which also may be referred to as false alarms or false positives). In some implementations, an object may be identified as possible contraband through the properties of its atomic density (which also may be referred to as bulk density) and atomic weight. Once identified as possible contraband, the object is subjected to radar tomography to confirm or dispel the proposition that the object may be contraband. In one example, both shampoo and explosive material may be identified as contraband through the use of x-ray imaging. Shampoo can be distinguished from explosive material through the use of radar tomography. Since shampoo has high dielectric properties and high loss properties, while explosive substances may have high dielectric properties and low loss properties. In another example, the use of radar tomography with conventional X-ray may helps to minimize false alarms due to foodstuffs including moisture. Because the dielectric constant of water is about 30 times higher than other materials, radar tomography can distinguish foodstuffs from contraband based on the dielectric property when contraband does not include a foodstuff.

More particularly, the target 1010 is subjected to x-ray scanning 1020, which may include, for example, conventional x-ray images, computerized tomography (CT), or backscatter x-ray images. The results of the x-ray scanning are used by the radar tomography process 1030 to further analyze the target 1010 for contraband. In the example process 1000, a location 1025 relative to the target is identified by the x-ray scanning 1020 and provided to the radar tomography process 1030 to help focus the direction of radar signal transmission. Generally, the location identifies an object included in or near the target. The location may be provided in x,y coordinates or x,y,z coordinates relative to the target where the coordinates outline the boundaries of an object in or near the target. The ability of a scanning process (here, the x-ray scanning 1020) to identify the location within a target space for analysis by a radar tomography process may help improve the accuracy of, and reduce the time required to conduct, a radar tomography process.

The radar tomography process 1030 may include transmitting stepped-frequency or swept-frequency radar signals. The radar tomography process 1030 may include detecting deflected portions of the radar signals and/or detecting radar signals that pass through the location of the object. The radar tomography process 1030 may process the detected radar signals to detect dielectric properties of an object identified by the location provided by the x-ray scanning process 1020, as described previously. Additionally or alternatively, the radar tomography process 1030 may process radar signals that pass through the location of the object to detect loss properties of the object.

A determination 1035 is made as to whether contraband is present in the location based on the x-ray scanning 1020 and the radar tomography process 1030. For example, an object included at or near the target may be determined to be contraband or a candidate for further search. The determination may be made, for example, based on the object's atomic density or atomic weight properties determined by the x-ray scanning 1020 and based on the object's dielectric and/or loss properties determined by radar tomography process 1030.

In some implementations, the location of multiple objects included in or near the target 1010 may be passed to the radar tomography process 1030 for further analysis. In some implementations, only an object or objects identified as contraband by the x-ray scanning 1020 are passed to the radar tomography process 1030. Alternatively, the location of all objects (regardless of whether an object is identified as contraband) identified in or near the target 1010 by the x-ray scanning 1020 may be passed to the radar tomography process 1030.

FIG. 11 illustrates a plan view of an exemplary system 1100 capable of using computerized x-ray tomography and computerized radar tomography to scan a target to detect contraband. More particularly, the example system 1100 includes a target 1110, which in this example represents an item of luggage, which includes objects 1112A-1112C. As illustrated, the target 1110 is located on a conveyer belt 1115 that transports the target 1110 through the system 1100 along the direction 1117. The target 1110 is shown within the x-ray tomography device 1120 having a curtain 1121 and an x-ray source 1122 that is configured to generate x-rays 1124. The x-rays 1124 interact with objects 1112A-1112C after passing through a surface of the target 1110 in which objects 1112A-1112C are located. X-rays 1124 that are not absorbed by the objects 1112A-1112C are sensed by the detector 1125. Detection of the x-ray radiation that is not absorbed by the objects 1112A-1112C allows determination of some characteristics of the materials that make up the objects 1112A-1112C. For example, a characteristic related to the atomic density and/or atomic weight of the materials that make up the objects 1112A-1112C may be determined based on the absorption of x-ray radiation by the materials. The atomic density and/or atomic weight may be used by imaging system 1128 to determine whether the objects 1112A-1112C include contraband. In some implementations, human-viewable images of the objects 1112A-1112C may be generated and displayed on the imaging system 1128.

The imaging system 1128 may include digital electronic circuitry, computer hardware, firmware, software, or in combinations of these elements. The imaging system 1128 may include one or more computer processors, and computer programs or another type of instructions tangibly embodied in machine-readable media or in a machine-readable storage device for execution by one or more programmable processors. The imaging system 1128 may include a display device, e.g., a CRT (cathode ray tube) or LCD (liquid crystal display) monitor, for displaying information and/or images to the operator. Other types of devices may be used to provide information to the operator, for example, feedback provided to the operator may be any form of sensory feedback, e.g., visual feedback, auditory feedback, or tactile feedback.

The target 1110 is moved by the conveyer belt to the radar tomography device 1130. The target 1110 may be moved to the radar tomography device 1130 based on, for example, completion of the x-ray scan, detection of contraband, or operator control.

The radar tomography device 1130 includes a series of elements that form a circumference 1135, which may be an implementation of circumference 150 of elements described previously with respect to FIG. 1; a transmit element (not shown), which emits a radar signal in the direction of one of the objects 1112A-1112C that is the subject of the radar tomography scan; and multiple receive elements located along the circumference of elements 1135. The radar signal transmitted by the radar tomography device 1130 is transmitted toward the location of the subject object 1112A, 1112B or 1112C. To do so, the radar tomography device 1130 uses a location relative to the target 1110 determined based on the x-ray images such that the location corresponds to the subject object 1112A, 1112B or 1112C.

As described previously, multiple receiving structures detect portions of the radar signal. The detected portions are processed to generate processed data including information associated with amplitudes and phases of the detected portions, and with the locations of the receiving structures at which the detected portions were detected. The processed data is analyzed to determine dielectric properties corresponding to particular positions. The dielectric properties are used to determine whether the subject object 1112A, 1112B or 1112C includes or is near contraband. The processed data may be used to generate an image for display on imaging system 1128.

Additionally or alternatively, multiple receiving structures may detect radar signals transmitted through the subject object 1112A, 1112B or 1112C. The amount of loss of the radar signal that is detected may be used to determine a loss property of the material of the subject object 1112A, 1112B or 1112C. The amount of loss may be used in addition to, or in lieu of, the dielectric properties of the subject object 1112A, 1112B or 1112C to determine whether the subject object 1112A, 1112B or 1112C includes or is near contraband.

In some implementations, a visual and/or audio alert may be generated based on the detection of contraband. In one example, an audible beep may sound. In another example, a visual display presented on the imaging system 1128 may be colorized to identify the object 1112A, 1112B or 1112C that has been identified as contraband or an object warranting further search.

Figure 12A:
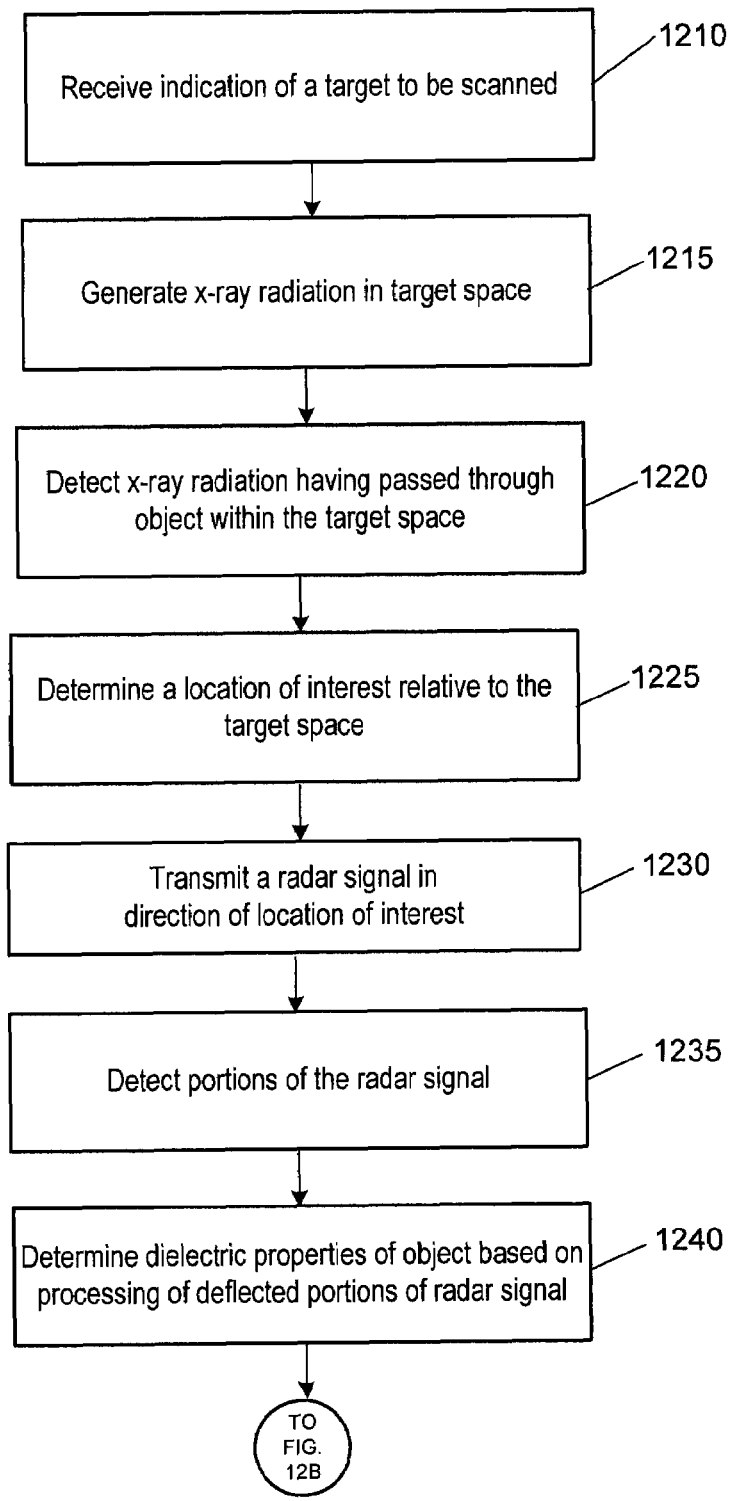
Figure 12B:
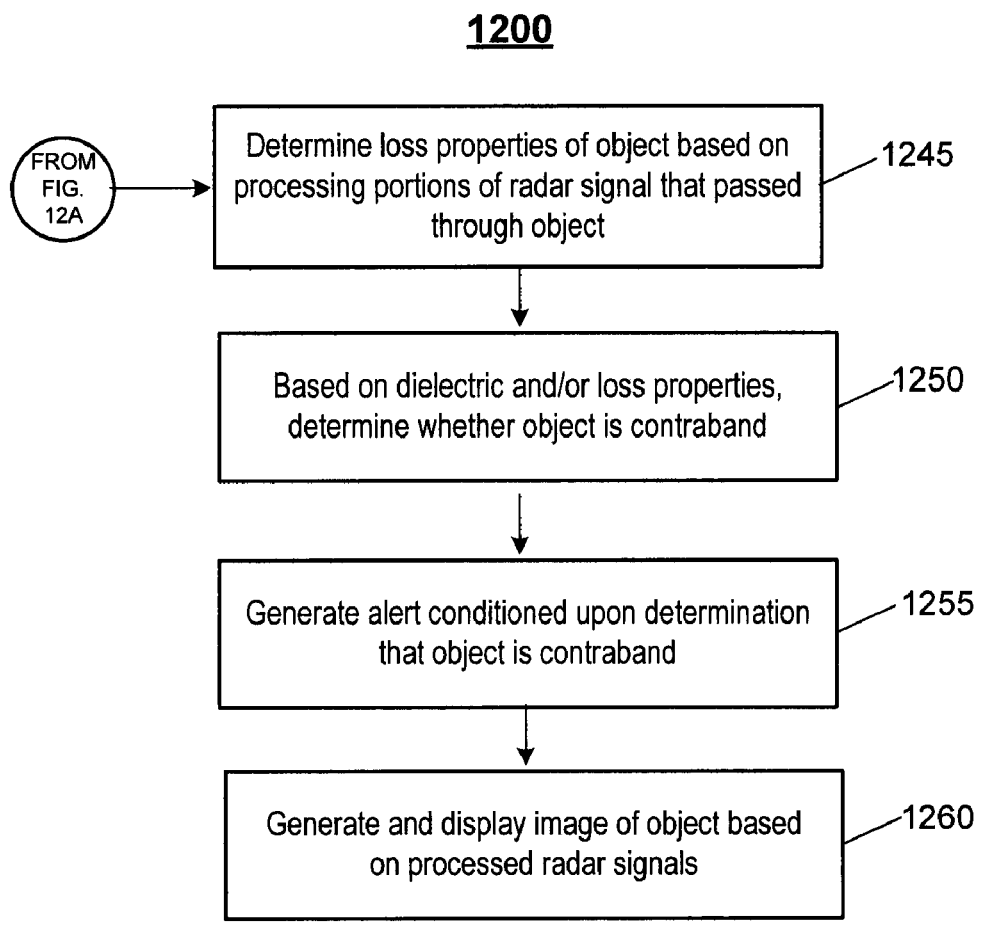

FIGS. 12A and 12B shows another exemplary process 1200 for detecting contraband by scanning a target using both x-rays and radar signals. The process 1200 may be performed by an imaging system, such as the example system 1100 described previously with respect to FIG. 11.

Referring to FIG. 12A, the process 1200 includes receiving an indication of a target to be scanned (step 1210). In one example, the imaging system may receive operator input initiating the process 1200 when a target is positioned for scanning. In another example, the imaging system may detect the presence of a target, such as a container or person to be scanned.

The imaging system generates x-ray radiation in the target space (step 1215). This may be accomplished, for example, by causing an x-ray source, such as source 1122 described previously with respect to FIG. 11, to generate x-ray radiation in the target space.

The imaging system detects x-ray radiation that has passed through an object in the target space (step 1220). This may be accomplished, for example, as described previously with respect to x-ray detector 1125 of FIG. 11.

The image system determines, based on the detected x-radiation that was not absorbed by an object in the target space, a location of interest relative to the target space (step 1225). The location of interest corresponds to the object in the target space. The location of interest may be determined based on the identification of an object within the target space. Additionally or alternatively, the location of interest may be determined based on an atomic density, an atomic weight or other property for an object within the target space that can be determined by using x-ray radiation. In some implementations, the object's property or properties determined by using x-ray radiation may be used to identify potential contraband. In one example, an atomic density and/or atomic weight of the object may be compared with corresponding information (e.g., atomic density, atomic weight) for contraband. The location of interest may be expressed in terms of x,y coordinates relative to a two-dimensional x-ray image or x,y,z coordinates relative to a three-dimensional x-ray image. The x-ray image may be processed to identify a location relative to the target space.

The imaging system transmits a radar signal in the direction of the location of interest relative to the target space (step 1230). This may be accomplished, for example, by transmitting a radar signal based on x,y coordinates or x,y,z coordinates relative to the target space where the coordinates outline the boundaries of a location of interest. The boundaries of the location of interest may correspond to the edges of an object in the target space. The radar signals may include stepped-frequency or swept-frequency radar signals. The transmission of the radar signal, for example, may be accomplished as described previously with respect to step 510 of FIG. 5.

The imaging system detects portions of the radar signal (step 1235). The imaging system may detect deflected portions of the radar signal, for example, as described previously with respect to step 520 of FIG. 5. In another example, the imaging system may detect portions of the radar signal that has passed through the object.

The imaging system determines dielectric properties of the object based on processing the deflected portions of the radar signal (step 1240). This may be accomplished, for example, as described previously with respect to steps 530 and 550 of FIG. 5.

Referring also to FIG. 12B, the imaging system determines loss properties of the object based on processing portions of the radar signal that passed through the object (step 1245).

The imaging system determines whether the object is contraband based on dielectric and/or loss properties (step 1250). For example, the dielectric and loss properties of the object may be compared with dielectric and loss properties of known substances. In some implementations, the dielectric properties may be compared to a range of dielectric properties of known substances, as may loss properties.

Differing characteristics of objects to be scanned, or differing characteristics to be searched for while scanning, may be conducive to using one property over the other property, or using both properties. For example, peanut butter and chocolate both have dielectrics that are similar to the dielectrics of some explosives, whereas the loss property of both peanut butter and chocolate are dissimilar to the loss properties of the explosives. Thus, using both dielectric and loss properties enables peanut butter and chocolate to be distinguished from explosives, whereas using only a dielectric property may not allow them to be distinguished.

The imaging system generates an alert conditioned upon determination that the object is contraband (step 1255). The imaging system may generate and display an image of the object based on processed radar signals (step 1260). This may be accomplished, for example, by aligning the x-ray tomography images with radar tomography images based on correspondence of the images with the target space. In some implementations, pattern-recognition techniques may be applied to the generated image. In one example, patterns representing known shapes of contraband may be compared with the generated image to help improve the accuracy of detecting contraband. In another example, patterns representing known shapes of items that are commonly mistaken for contraband may be compared with the generated image.

The radar tomography process, such as the process described with respect to steps 1230-1260, need not necessarily be performed with, or sequentially to, an x-ray tomography process. For example, in some implementations, an imaging process may begin based on receipt of a location of interest to be used to target radar signals. In such a case, the radar tomography process may be performed without performing the x-ray tomography process.

In another example of a security application of radar tomography, a commercially available radar scanner, such as a security scanning portal from L-3 SafeView of Santa Clara, Calif., may be used to implement radar tomography described above. In one implementation, a wavelength of 28 GHz may be used by the scanner to take 64 different images (each of which may be referred to as a slice) of a person or a piece of luggage (which also may be referred to as a bag). In general, scanning a person uses the reflectivity of radar signals with respect to the body and concealed liquids and gels. Clothing has little or virtually no liquid content and so has a very low dielectric. The radar signal passes through clothing and reflects back off of the skin and other objects, making the clothing appear substantially transparent.

For scanning a person, the strongest slices with the most backscatter may be used to construct an image of the person. Alternatively or additionally, most or all of the slices may be used to reconstruct the image of the person. An image of a person may be adjusted to protect the person's privacy, such as by obscuring the face so the person is not identifiable or hiding the person's private areas.

The techniques and concepts described above can be used to detect liquids, such as liquids in luggage, or on or near a person. The amount of radar signal that is reflected by liquid may be used to detect liquids. For example, liquids that are on or near a person may be detected through the use of radar tomography when the liquid does not have a high water content. Liquids that have a high water content, such as water and shampoo, may have similar reflective properties to the human body and, thus, may be more difficult to distinguish from a person. Liquids that do not have a high water content, such as oils, may be more readily detected based on reflected signal strength.

The techniques and concepts described above also could be used in medical applications. With regard to one example of a medical application, a frequency of 2 to 4 GHz in a radar tomography system described above is able to penetrate the surface of the skin a few millimeters and allows for the taking of an image of the entire human body, generally in a few seconds. The resulting image may be used to search for skin cancer, which could be detected based on a significant blood supply being close to the surface of the skin.

Useful results still could be achieved if steps of the disclosed techniques or concepts are performed in a different order and/or if components in the disclosed systems are combined in a different manner and/or replaced or supplemented by other components.

Thus, particular implementations have been described. Other implementations are within the scope of the following claims.

What is claimed is:

1. A method of detecting contraband, the method comprising:
   receiving a location of interest, the location of interest corresponding to a location in a target space;
   transmitting a radar signal in the direction of the location of interest;
   detecting, with multiple receiving structures, deflected portions of the radar signal;
   processing the detected deflected portions to generate processed data including information associated with amplitudes and phases of the detected deflected portions, and with the locations of the receiving structures at which the detected deflected portions were detected;
   analyzing the processed data to determine information corresponding to dielectric properties, the dielectric properties corresponding to particular positions within the target space; and
   determining, based on the dielectric properties, whether contraband is present in the target space.

2. The method of claim 1 further comprising:
   transmitting x-ray radiation in the target space;
   detecting x-ray radiation in the target space; and
   determining, based on the detected x-ray radiation, the location of interest.

3. The method of claim 2 further comprising determining a characteristic related to absorption of x-rays for a portion of the target space,
   wherein determining the location of interest comprises using the characteristic related to absorption of x-rays for the portion of the target space.

4. The method of claim 3 wherein determining whether contraband is included in the target space comprises determining whether contraband is included in the target space based on the dielectric properties and the characteristic related to absorption x-rays for the portion of the target space.

5. The method of claim 1 further comprising:
   detecting, with multiple receiving structures, portions of the radar signal that passed through an object corresponding to the location of interest;
   processing the detected portions of the radar signal that passed through the object to determine information corresponding to loss properties, the loss properties corresponding to the object within the target space; and
   determining whether contraband is included in the target space based on the dielectric properties and the loss properties.

6. The method of claim 5 further comprising determining a characteristic related to absorption x-rays fore portion of the target space,
   wherein:
      determining the location of interest comprises using the characteristic related to absorption of x-rays for the portion of the target space, and
      determining whether contraband is included in the target space comprises using the dielectric properties, the loss properties and the characteristic related to absorption of x-rays for the portion of die target space.

7. The method of claim 1 further comprising performing operations conditioned upon a determination that the dielectric properties are consistent with dielectric properties of contraband, the operations comprising:
   detecting, with multiple receiving structures, portions of the radar signal that passed through an object corresponding to the location of interest;
   processing the detected portions of the radar signal that passed through the object to determining information corresponding to loss properties, the loss properties corresponding to the object within the target space; and
   determining whether contraband is included in the target space based on the dielectric properties and the loss properties.

8. The method of claim 1 wherein the contraband comprises at least one of an explosive, a liquid and a foodstuff.

9. The method of claim 1 wherein the contraband is included on or near a person.

10. The method of claim 1 wherein the contraband is included in a container that is scanned independently of a person.

11. The method of claim 1 wherein transmitting a radar signal comprises transmitting one of a stopped-frequency radar signal or a swept-frequency radar signal.

12. The method of claim 1, wherein the location of interest determines a region of interest that is smaller than the target space, and transmitting a radar signal in the direction of the location of interest comprises transmitting the radar signal in the direction of the region of interest, and further comprising generating, from the deflected portions of the radar signal, an image of the region of interest.

13. A system for detecting contraband, the system comprising:
   a processor configured to receive a location of interest, the location of interest corresponding to a location in the target space;
   one or more transmission structures configured to transmit a radar signal in the direction of the received location of interest;
   receiving structures each configured to detect deflected portions of the radar signal;
   a processor configured to process the detected portions to generate processed data including information associated with amplitude, phase, and the receiving structure in which the reflected portion was detected;
   an analyzer configured to analyze the processed data to determine information corresponding to dielectric properties of the object and an associated position, within the target space, of the information corresponding to dielectric properties; and
   a detector configured to determine based on the dielectric properties whether contraband is present in the target space.

14. The system of claim 13 further comprising an x-ray device comprising:
   a first source configured to produce x-ray radiation;
   a first detector configured to detect x-ray radiation; and
   a location detector configured to determine, based on the detected x-ray radiation, the location of interest within the target space.

15. The system of claim 14 further comprising a radar tomography device comprising the one or more transmission structures, the receiving structures, the processor and the analyzer,
   wherein the x-ray device is configured to send the location of interest within the target space to the radar tomography device.

16. The system of claim 13 further comprising a radar tomography device comprising the one or more transmission structures, the receiving structures, the processor, and the analyzer, and configured to:
   detect, with multiple receiving structures, portions of the radar signal that passed through an object corresponding to the location of interest;
   process the detected portions of the radar signal that passed through the object to generate processed data including information associated with amplitudes and phases of the deflected Portions, and with the locations of the receiving structures at which the deflected portions were detected;
   analyze the processed data to determine information corresponding to loss properties, the loss properties corresponding to the object within the target space; and
   determine whether contraband is present in the target space based on the dielectric properties and the loss properties.

17. The system of claim 13 wherein the contraband comprises at least one of an explosive, a liquid and a foodstuff.

18. The system of claim 13 wherein the contraband is included on or near a person.

19. The system of claim 13 wherein the contraband is included in a container that is scanned independently of a person.

20. The system of claim 13 wherein the one or more transmission structures are configured to transmit one of a stepped-frequency radar signal or a swept-frequency radar signal.

21. A method of detecting contraband, the method comprising:
   receiving a location of interest, the location of interest corresponding to a location in a target space;
   transmitting a radar signal in the direction of the location of interest;
   detecting, with multiple receiving structures, portions of the radar signal;
   processing the detected portions to generate information corresponding to dielectric or loss properties, the properties corresponding to particular positions within the target space; and determining whether contraband is present in the target space based on the determined properties.

22. A method of generating an image of living tissue, the method comprising:
- receiving location of interest, the location of interest corresponding to a location in a target space that includes living tissue;
- transmitting a radar signal toward the region of interest and through the living tissue;
- detecting, with multiple receiving structures, deflected portions of the radar signal;
- processing the detected deflected portions to generate processed data including information associated with amplitudes and phases of the detected deflected portions, and with the locations of the receiving structures at which the detected deflected portions were detected;
- analyzing the processed data to determine information corresponding to dielectric properties, the dielectric properties corresponding to particular positions of the living tissue; and generating, based on the dielectric properties of the living tissue, an image of the living tissue.

23. The method of claim 22 Further comprising detecting, based on the dielectric properties of the living tissue, an anomalous portion of living tissue.

24. The method of claim 23 wherein detecting an anomalous portion of living tissue comprises detecting, based on a difference of dielectric properties of a portion the living tissue from the dielectric properties of another portion of the living tissue, an anomalous portion of living tissue.

25. The method of claim 23 wherein the anomalous portion of living tissue comprises a tumor or a precancerous growth.

* * * * *

UNITED STATES PATENT AND TRADEMARK OFFICE
CERTIFICATE OF CORRECTION

| | | |
|---|---|---|
| PATENT NO. | : 7,671,784 B2 | Page 1 of 1 |
| APPLICATION NO. | : 11/852623 | |
| DATED | : March 2, 2010 | |
| INVENTOR(S) | : William Steinway et al. | |

It is certified that error appears in the above-identified patent and that said Letters Patent is hereby corrected as shown below:

Claim 4
At col. 17, line 3, after "absorption", insert --of--.

Claim 6
At col. 17, line 16, replace "fore" with --for a--.

At col. 17, line 25, replace "die" with --the--.

Claim 7
At col. 17, line 35, replace "determining" with --determine--.

Claim 11
At col. 17, line 49, replace "stopped-frequency" with --stepped-frequency--.

Claim 16
At col. 18, line 37, replace "Portions" with --portions--.

Claim 22
At col. 19, line 5, after "receiving", insert --a--.

Claim 23
At col. 20, line 6, replace "Further" with --further--.

Claim 24
At col. 20, line 11, after "portion", insert --of--.

Signed and Sealed this

Twenty-second Day of June, 2010

David J. Kappos
*Director of the United States Patent and Trademark Office*